United States Patent
Kao et al.

(10) Patent No.: US 12,201,282 B2
(45) Date of Patent: *Jan. 21, 2025

(54) ENDOSCOPE ASSEMBLY AND ENDOSCOPE SYSTEM HAVING THE SAME

(71) Applicants: Hong So Kao, Taipei (TW); Chin Piao Chang, Zaoqiao Township (TW)

(72) Inventors: Hong So Kao, Taipei (TW); Chin Piao Chang, Zaoqiao Township (TW)

( * ) Notice: Subject to any disclaimer, the term of this patent is extended or adjusted under 35 U.S.C. 154(b) by 0 days.

This patent is subject to a terminal disclaimer.

(21) Appl. No.: 17/588,638

(22) Filed: Jan. 31, 2022

(65) Prior Publication Data
US 2022/0240914 A1 Aug. 4, 2022

(30) Foreign Application Priority Data

Feb. 3, 2021 (TW) ................... 110201346
Oct. 4, 2021 (TW) ................... 110136834

(51) Int. Cl.
*A61B 1/00* (2006.01)
*A61B 1/05* (2006.01)
(Continued)

(52) U.S. Cl.
CPC .... *A61B 17/00234* (2013.01); *A61B 1/00016* (2013.01); *A61B 1/00045* (2013.01);
(Continued)

(58) Field of Classification Search
CPC ............ A61B 1/00016; A61B 1/00045; A61B 1/00096; A61B 1/00165; A61B 1/00179;
(Continued)

(56) References Cited

U.S. PATENT DOCUMENTS 6,425,910 B1 7/2002 Hugueny et al.
11,033,255 B2 6/2021 Furlong et al.
(Continued)

FOREIGN PATENT DOCUMENTS

DE 102015103214 A1 * 9/2016
TW 200733932 A 9/2007
(Continued)

OTHER PUBLICATIONS

Search Report, Taiwan counterpart Application No. 110136834, issued Apr. 21, 2022, English translation.
(Continued)

*Primary Examiner* — Timothy J Neal
*Assistant Examiner* — William B Chou
(74) *Attorney, Agent, or Firm* — Blank Rome LLP (57) ABSTRACT

An endoscope assembly includes a base module, an injection needle, and an image sensing unit. The base module includes an illumination input end. The injection needle is tubular, is connected to the base module, and has a needle shaft. The needle shaft has a bevel surface that is formed on a distal end thereof. The image sensing unit includes a tube portion that extends inside the needle shaft, and an image sensor that is connected to a distal end of the tube portion and that is adjacent to the bevel surface of the needle shaft. Additionally, a passage is formed between the tube portion and an inner surface of the needle shaft.

10 Claims, 6 Drawing Sheets

(51) Int. Cl.
*A61B 1/06* (2006.01)
*A61B 1/07* (2006.01)
*A61B 17/00* (2006.01)

(52) U.S. Cl.
CPC ...... *A61B 1/00124* (2013.01); *A61B 1/00128* (2013.01); *A61B 1/05* (2013.01); *A61B 1/0684* (2013.01); *A61B 1/07* (2013.01)

(58) Field of Classification Search
CPC ......... A61B 1/05; A61B 1/07; A61B 17/3415; A61B 17/3478; A61B 1/015
See application file for complete search history.

(56) References Cited

U.S. PATENT DOCUMENTS

| | | | | |
|---|---|---|---|---|
| 2004/0059293 | A1* | 3/2004 | Chu | A61J 15/0057 604/174 |
| 2008/0064925 | A1* | 3/2008 | Gill | A61B 1/00167 600/109 |
| 2008/0195128 | A1* | 8/2008 | Orbay | A61B 17/320016 600/183 |
| 2012/0172663 | A1 | 7/2012 | Perretta et al. | |
| 2014/0257203 | A1* | 9/2014 | Favier | A61B 17/3403 72/364 |
| 2016/0235286 | A1* | 8/2016 | Chiang | A61B 1/00167 |
| 2019/0133430 | A1 | 5/2019 | Inglis et al. | |
| 2020/0000330 | A1 | 1/2020 | Ikeda et al. | |
| 2020/0170672 | A1* | 6/2020 | Einarsson | A61B 1/015 |
| 2020/0178769 | A1* | 6/2020 | Henley | A61B 17/3478 |
| 2020/0214739 | A1* | 7/2020 | Shi | A61B 1/07 |
| 2020/0305703 | A1* | 10/2020 | Bala | A61B 1/00105 |
| 2022/0211252 | A1* | 7/2022 | Ouyang | A61B 10/04 |
| 2022/0240961 | A1 | 8/2022 | Kao et al. | |

FOREIGN PATENT DOCUMENTS

| | | |
|---|---|---|
| TW | 200744517 A | 12/2007 |
| TW | 201919537 A | 6/2019 |
| WO | 2021/016626 A1 | 1/2021 |

OTHER PUBLICATIONS

Search Report appended to an Office Action, issued in Taiwan counterpart Application No. 110136442 by the TIPO issued Jun. 23, 2022 with an English translation.

Search Report issued in European counterpart Application No. 22154089.1 by the EPO on Jul. 1, 2022.

* cited by examiner

ENDOSCOPE ASSEMBLY AND ENDOSCOPE SYSTEM HAVING THE SAME

CROSS-REFERENCE TO RELATED APPLICATION

This application claims priority to Taiwanese Utility Model Application No. 110201346, filed on Feb. 3, 2021, and Taiwanese Invention Patent Application No. 110136834, filed on Oct. 4, 2021.

FIELD

The disclosure relates to an endoscope, and more particularly to an endoscope assembly and an endoscope system using the endoscope assembly.

BACKGROUND

Conventional medical endoscopic devices are fitted with various tools and used to examine the interior of a patient's body. A variety of endoscopic devices have been developed according to the requirements of various medical procedures such as thoracoscopy, laparoscopy, laparoscopic bile duct surgery, and pelvic laparoscopy. The conventional endoscope has an image sensor attached to either a soft tube or a rigid pipe and is inserted into the body cavity of the patient during a medical examination. A light source is provided through the endoscope to illuminate an area around the image sensor so that image data may be captured and transmitted directly to the observer or transmitted to an electronic device that is used by a doctor for making a diagnosis. When the diagnosis is made by the doctor, the conventional endoscope is extended into the patient's body cavity by making an incision on the patient, and the conventional endoscope is used to locate a surgical area for a surgeon to perform a surgical operation based on the diagnosis. Next, the conventional endoscope is secured in a position where it can continuously monitor the surgical area, and an injection needle or other surgical instrument is extended to the surgical area alongside the conventional endoscope to perform surgical operations based on the doctor's diagnosis. The operation may be a medical injection, cauterization, or surgical resection etc. However, due to the limited size of the incision and the limited space of the patient's body cavity, the other surgical instruments may interfere with the endoscope, and the endoscope may be displaced from monitoring the surgical area when operating the other surgical instruments, thereby causing the surgeon to lose sight of the surgical area and having to reposition the endoscope. On the other hand, the other surgical instruments or injection needles required for the surgical operation must be inserted into the patient's body cavity in some way, and will either need to be inserted via the same incision as the endoscope and thereby making the incision larger, or by making a new incision on the patient; the enlarged incisions will most likely require sutures to close, and an increase in the size and number of incisions increases the length of the patient's postoperative recovery period.

SUMMARY

Therefore, an object of the disclosure is to provide an endoscope assembly that can alleviate at least one of the drawbacks of the prior art.

According to one aspect of the disclosure, an endoscope assembly includes a base module, an injection needle, and an image sensing unit. The base module includes an illumination input end. The injection needle is tubular, is connected to the base module, and has a needle shaft. The needle shaft has a bevel surface that is formed on a distal end thereof. The image sensing unit includes a tube portion that extends inside the needle shaft, and an image sensor that is connected to a distal end of the tube portion and that is adjacent to the bevel surface of the needle shaft. A passage is formed between the tube portion and an inner surface of the needle shaft.

Another object of the disclosure is to provide an endoscope system having the abovementioned endoscope assembly.

According to another aspect of the disclosure, an endoscope system includes the abovementioned endoscope assembly and an output unit. The base module of the endoscope assembly further has an output end. The output unit is connected to the output end of the base module of the endoscope assembly, and has a bus that is connected to the image sensing unit via a data connection, a processor that is connected to the bus via a data connection, and a display panel that is electrically connected to the processor. The bus is disposed for transmitting an image signal captured by the image sensor. The processor is disposed for receiving the image signal transmitted by the bus and for processing the image signal. The display panel is disposed for displaying the image signal processed by the processor.

BRIEF DESCRIPTION OF THE DRAWINGS

Other features and advantages of the disclosure will become apparent in the following detailed description of the embodiments with reference to the accompanying drawings, of which.

DETAILED DESCRIPTION

Before the disclosure is described in greater detail, it should be noted that where considered appropriate, reference numerals or terminal portions of reference numerals have been repeated among the figures to indicate corresponding or analogous elements, which may optionally have similar characteristics.

Referring to FIGS. 1 to 3, and FIG. 6, showing an embodiment of an endoscope system according to the present disclosure. The endoscope system includes an endoscope assembly 1, an output unit 231, an image reader 232, and a graphics processor 233 (see FIG. 6). The endoscope assembly 1 includes a base module 20, an injection needle 10, and an image sensing unit 21 that includes an image sensor 211.

Figure 1:
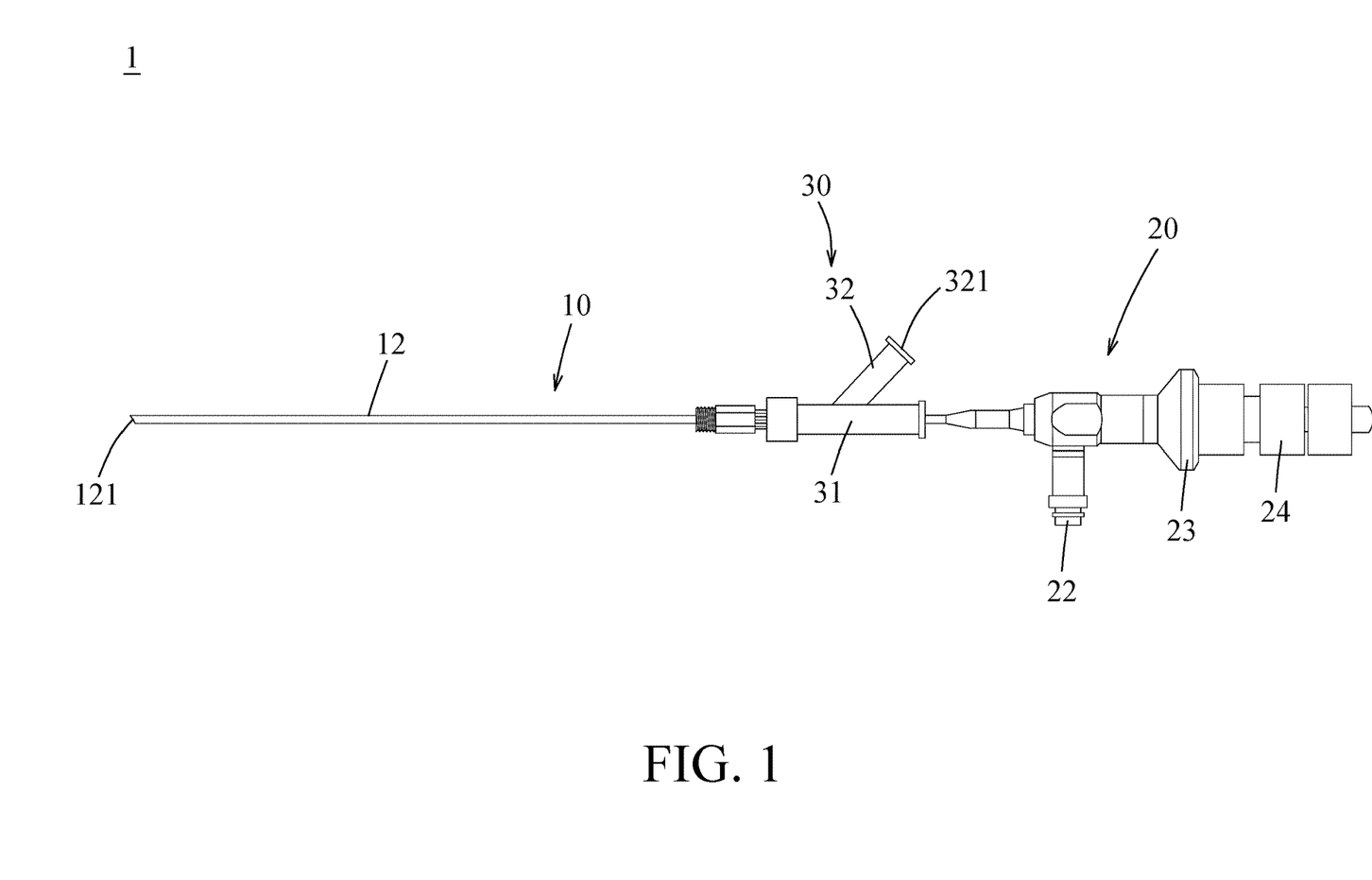
FIG. 1 is a schematic side view illustrating an endoscope assembly of an embodiment of an endoscope system according to the present disclosure.
Figure 2:
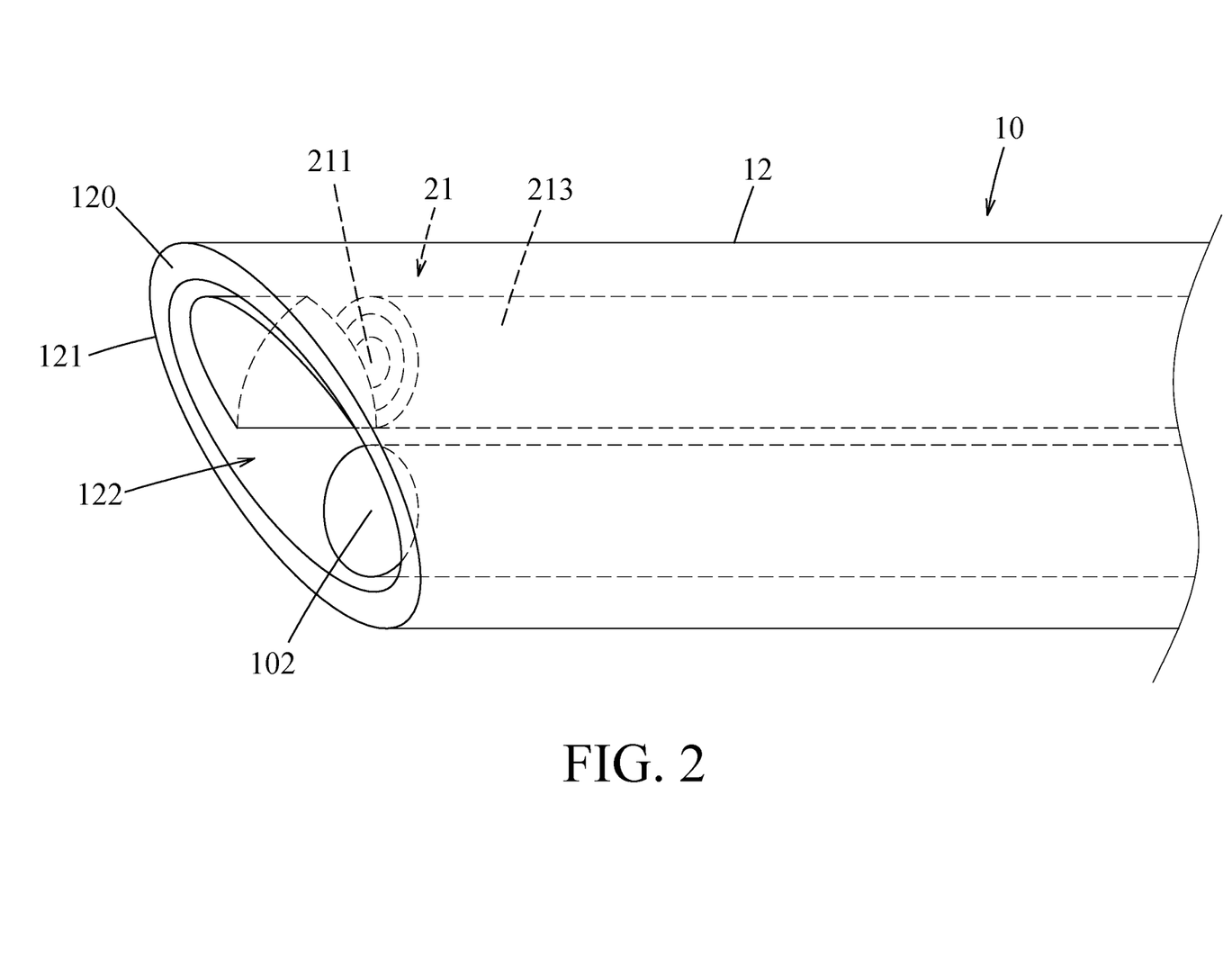
FIG. 2 is an enlarged fragmentary schematic and perspective view showing an injection needle of the endoscope assembly of the embodiment in a penetration mode.

Referring to FIGS. 1, and 2, the base module 20 includes an illumination input end 22, an output end 23 connected to the illumination input end 22, and a relay mechanism 24 connected to the output end 23. The output unit 231 is connected to the output end 23 of the base module 40 of the endoscope device 20. The illumination input end 22 is adapted to receive a light source conductor 101 that extends towards the image sensor 211. In this embodiment, the relay mechanism 24 is configured as one of an optical fiber light concentrator, a multimedia interface, and an LED light power source. Additionally, the output unit 231 can be connected to the output end 23 of the base module 20 via a wireless connection. In this case, the relay mechanism 24 can have a wireless communication module attached, or in cases where wireless connection is not required a traditional wired communication module may be substituted. The output unit 231, image reader 232, and graphics processor 233 can be connected to the output end 23 via the relay mechanism 24. However, the relay mechanism 24 can also be omitted in some embodiments. For example, the output unit 231 can be a head-mounted display (HMD), so that an operating surgeon may be provided with a live feed video captured by the image sensing unit 21.

The injection needle 10 is tubular, is connected to the base module 20, and has a needle shaft 12; the injection needle 10 further includes a Y-connector 30, and the needle shaft 12 is connected to the Y-connector 30 at an end of the Y-connector 30 that is distal from the base module 20. In this embodiment, the Y-connector 30 is removably connected to the base module 20 so that the injection needle 10 is replaceable; the injection needle 10 is therefore disposable and sterilizing the injection needle 10 after use will be unnecessary. However, it should be mentioned that the above mentioned configuration is not a limitation of this disclosure, and in other embodiments the injection needle 10 may be removably connected to the Y-connector 30 instead.

The injection needle 10 further includes a filler member 102. A passage 40 is formed between the tube portion 213 and an inner surface of the needle shaft 12. The Y-connector 30 includes a first branch tube 31, and a second branch tube 32 communicating with the first branch tube 31. The first branch tube 31 has two opposite ends that are respectively connected to the base module 20 and the needle shaft 12, and that fluidly communicate with the passage 40. The first branch tube 31 guides the light source conductor 101 from the output end 22 towards the image sensing unit 21 inside the needle shaft 12. The second branch tube 32 has an injection port 321 that is adapted for inlet of a pharmaceutical therethrough into the passage 40.

The needle shaft 12 of the injection needle 10 has a bevel surface 121 that is formed on a distal end thereof, and an end hole 122 that is formed in the bevel surface 121. The pharmaceutical that was inlet into the passage 40 is outlet through the end hole 122. In this embodiment, the image sensor 211 has an end surface that is perpendicular to an axis of the injection needle 10. The bevel surface 121 of the needle shaft 12 is inclined relative to the end surface of the image sensor 211, and forms a sharp tip 120 that can easily puncture a patient's skin. With the sharp tip 120 the injection needle 12 only makes a small wound when puncturing the patient, and the small wound facilitates postoperative recovery and will not require sutures to close. For example, the needle shaft 12 may be made of a stainless steel material and the outer diameter may range from 1.0 millimeters to 2.5 millimeters, so that the wound on the patient will be no larger than 2.5 millimeters, which will not require sutures to close and thereby facilitate the patient's recovery. The length of the injection needle 10 is in a range from 40 millimeters to 450 millimeters, and more optimally in a range from 60 millimeters to 300 millimeters.

Figure 3:
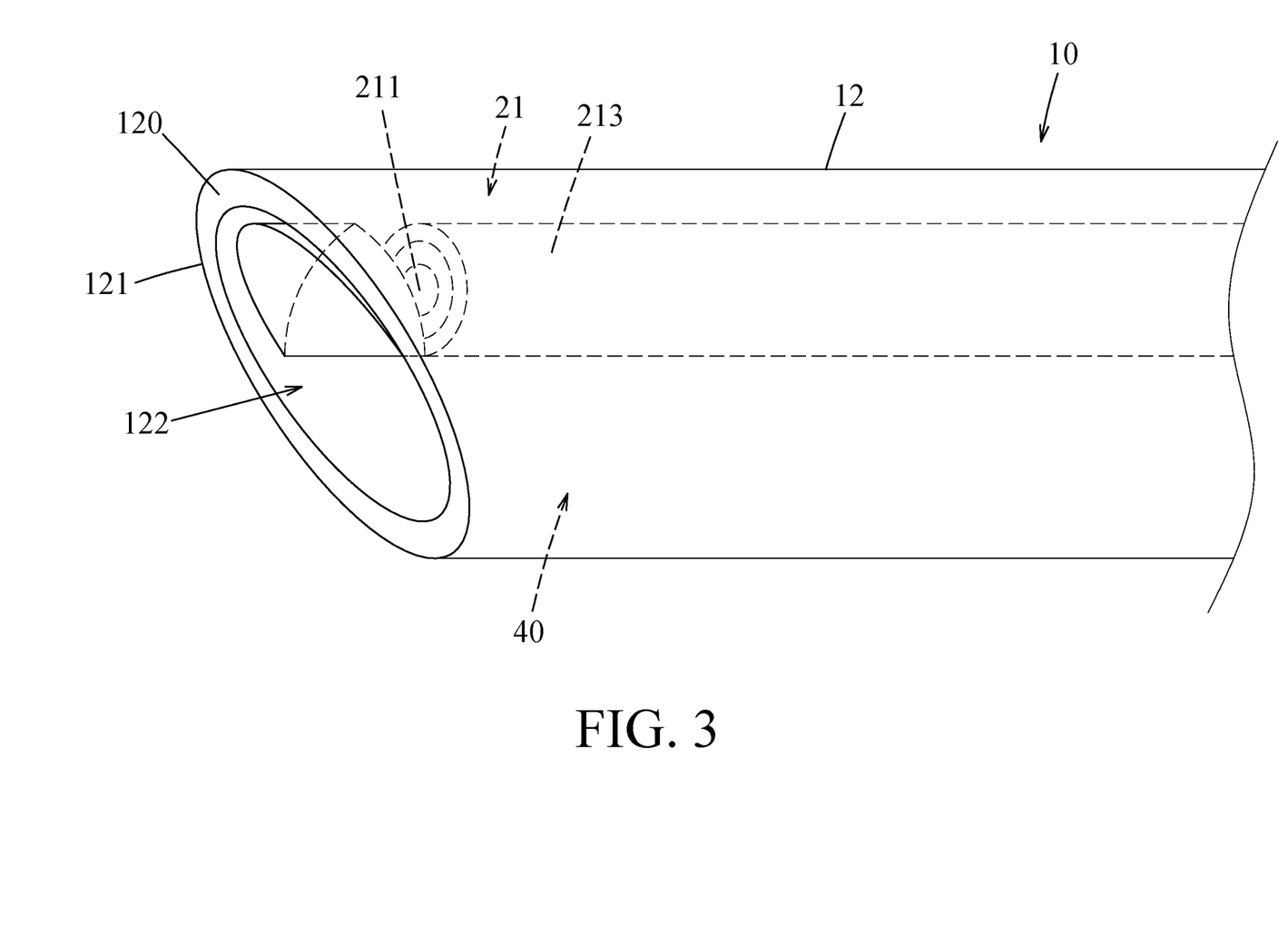
FIG. 3 is an enlarged fragmentary schematic and perspective view showing the injection needle of the endoscope assembly of the embodiment in an injection mode.

Referring to FIGS. 2 and 3, the image sensing unit 21 includes a tube portion 213 that extends inside the needle shaft 12, and the image sensor 211 is connected to a distal end of the tube portion 213 and is adjacent to the bevel surface 121 of the needle shaft 12. In this embodiment, the image sensor 211 may be a traditional optical camera used with a fiberscope, a charge-coupled device (CCD) image sensor, or a complementary metal-oxide semiconductor (CMOS) image sensor, but are not limited to these examples. The image sensor 211 may includes a processor (not shown) to process the image data before sending the image data to the output end 23.

Referring to FIGS. 1 to 3, the injection needle 10 is convertible between a penetration mode where the filler member 102 extends into the passage 40, and an injection mode where the filler member 102 is removed from the passage 40. When the injection needle 10 punctures the patient's skin it in the penetration mode, the patient's tissue is prevented from clogging the end hole 122 of the injection needle 10, and causing an uneven wound on the patient that is difficult to heal. Additionally it should be noted that if such clogging where to occur, it may prevent the outlet of the pharmaceutical from the end hole 122. On the other hand, when the injection needle 10 is in the injection mode it can be used to inject the pharmaceutical onto a surgical area, where the pharmaceutical will outlet from the end hole 122 of the injection needle 10. However, in other embodiments of the endoscope assembly 1, a soft tube (not shown) can be extended through the passage 40 and out of the end hole 122, so that surgical irrigation fluid (such as saline) may be used to irrigate the surgical area. Likewise the soft tube may also be used as a surgical drain to drain out the irrigation fluid and other bodily fluids. Additionally a second soft tube (not shown) may be extended through the passage 40 so that the surgical area may be drained as it is irrigated. Alternatively, other surgical instruments and devices necessary for a variety of surgical operation may be extended via the passage 40.

Figure 4A:
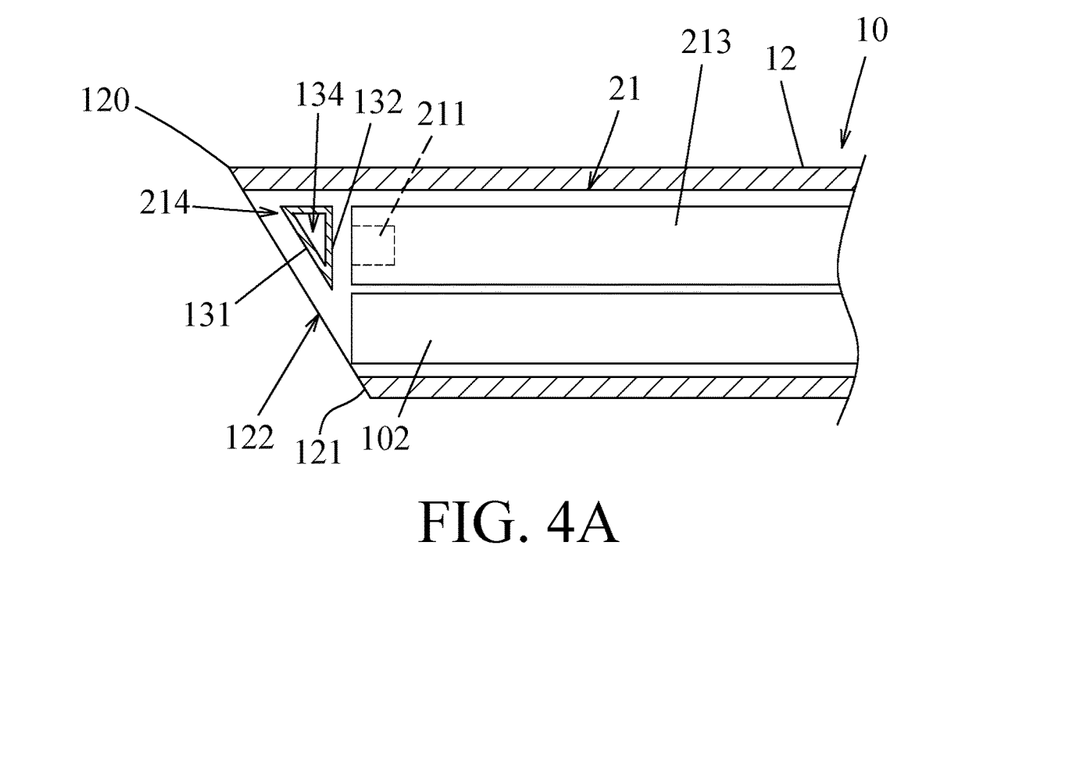
FIG. 4A is an enlarged fragmentary sectional view of the injection needle of the endoscope assembly of the embodiment.
Figure 4B:
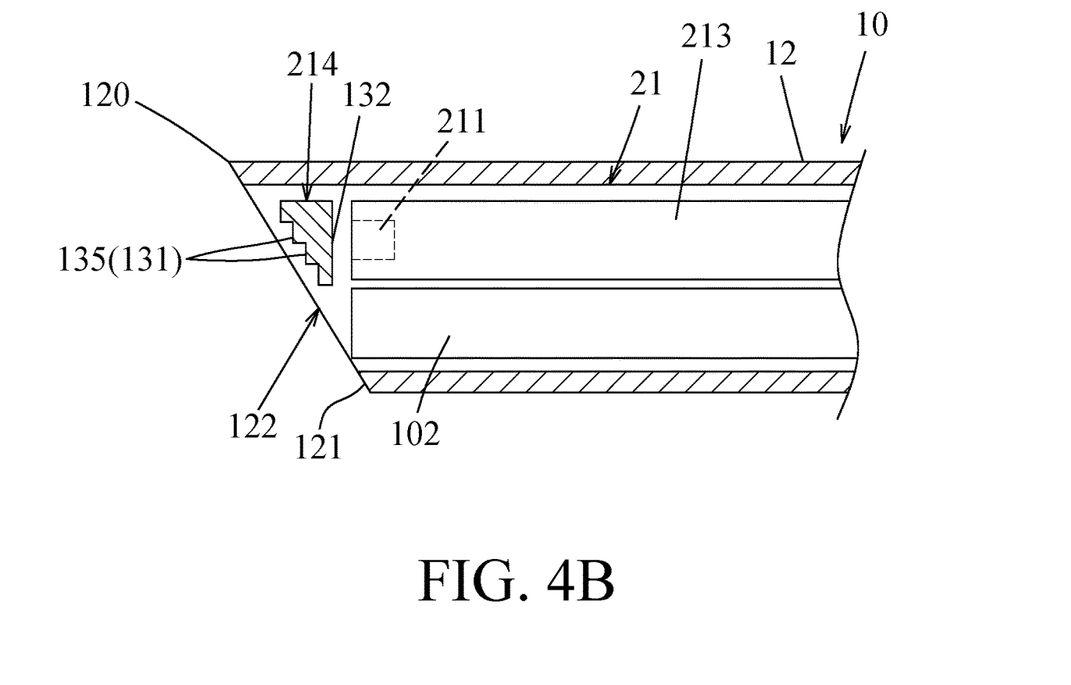
FIG. 4B is a view similar to FIG. 4A, but showing a variation of the injection needle of the endoscope assembly of the embodiment.

Referring to FIGS. 2, 4A, and 4B, the injection needle 10 further includes an optical component 214 mounted in the needle shaft 12 in front of the image sensor 211, under the sharp tip 120 and adjacent to the end hole 122. The optical component 214 is used to help the image sensor 211 resolve the surgical area. The optical component 214 is mounted under the sharp tip 120 so that it is sheathed away from directly impacting body tissue when the injection needle 24 is puncturing the patient's skin, which will prevent tearing of the patient's tissue. The wound on the patient will therefore be more even and the healing of the wound will be comparatively quicker than an uneven puncture wound. Additionally, this helps prevent tissue from building up in front of the image sensor 211 during the puncturing and will help to maintain a clear image of the surgical area. The optical component 214 is made from a transparent material (such as glass or plastics), and has a light incident side 131 mounted adjacent to and parallel to the bevel surface 121 of the needle shaft 12, and is adapted to guide light into the optical component 214. The optical component 214 further has a light emergent side 132 parallel to and facing the end surface of the image sensor 211 and adapted to guide light from the light incident side 131 toward the image sensor 211. In more detail, the optical component 214 is in a beveled frustoconical shape that is beveled at the same incline as the bevel surface 121 (as shown in FIGS. 4A, 4B). In this embodiment, the light incident side 131 and the light emergent side 132 of the optical component 214 forms an acute angle therebetween.

In this embodiment, the optical component 214 is structurally hollow, and has an inner space 134 between the light incident side 131 and the light emergent side 132. The light emergent side 132 is adapted to guide light that is incident on the light incident side 131 and that is refracted by the inner space 134 to be substantially perpendicular to the end surface of the image sensor 211. Specifically, the hollow structure of the optical component 214 generates minimal interference with light passing through the optical component 214 and refracted by the inner space 134.

Referring to FIG. 4B, showing another embodiment of the endoscope assembly 1 according to this disclosure. In this embodiment, the light incident side 131 is stepped, and has a plurality of spaced-apart first incident surfaces 135 that are parallel to the end surface of the image sensor 211 and and that are arranged in a direction parallel to the bevel surface 121 of the needle shaft 12. Each of the first incident surfaces 135 has a length that is not larger than one micrometer. In this embodiment, because the first incident surfaces 135 are micron sized in scale and arranged in a direction parallel to the bevel surface 121, a significant portion of incident light passes perpendicularly through the light incident side 131, the light emergent side 132 and onto the image sensor 211, and thereby reducing distortion of the image due to refraction.

Figure 5A:
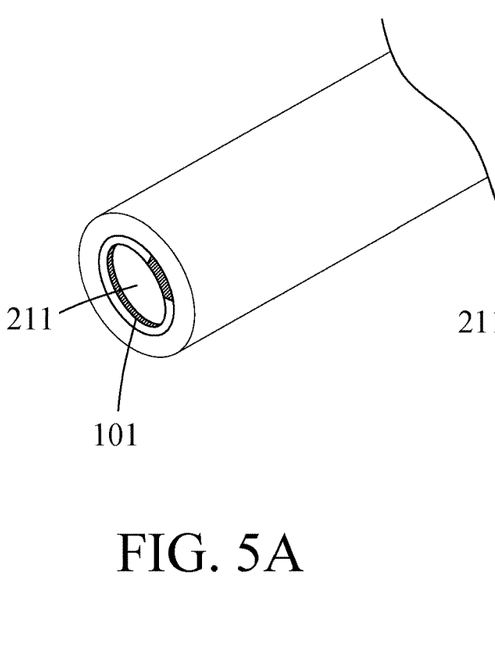
FIGS. 5A, 5B and 5C show variations of the configuration of a light source conductor.
Figure 5B:
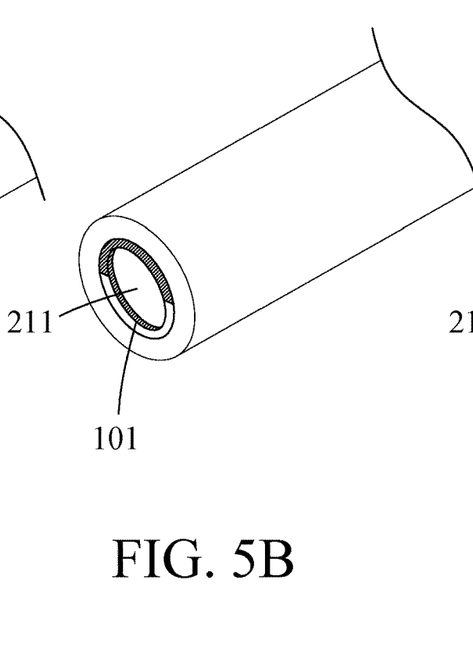
Figure 5C:
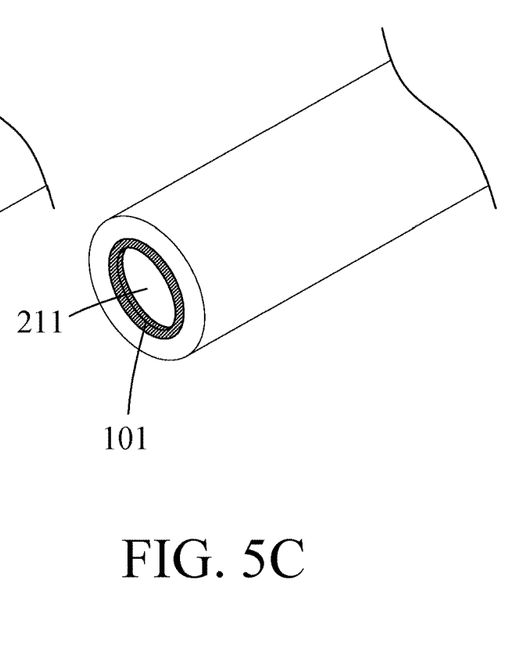

Referring to FIG. 2 and, the light source conductor 101 conducts the light source provided from the illumination input end 22. In this embodiment the light source conductor 101 is configured as a plurality of optical fiber strands that are arranged in a circle around a periphery of the image sensor 211. The optical fiber strands may be arranged in a full circle around the image sensor 211 as shown in FIG. 5C or arranged to be partially concentrated around one portion of the image sensor 211 as shown in FIGS. 5A and 5B. In other embodiments, the light source conductor 101 may be an LED light source (not shown) disposed adjacent to the bevel surface 121 of the needle shaft 12; in these embodiments, electrical wires running through the needle shaft 12 are used to power the LED light (not shown).

Referring to FIGS. 1 to 6, the output unit 231 has a bus 2311 that is connected to the image sensing unit 21 via a data connection, a processor 2312 that is connected to the bus 2311 via a data connection, and a display panel 2313 that is electrically connected to the processor 2312. The bus 2311 is disposed for transmitting an image signal captured by the image sensor 211, the processor 2312 is disposed for receiving the image signal transmitted by the bus 2311 and for processing the image signal, and the display device 2313 is disposed for displaying the image signal processed by the processor 2312. For example an image of the patient's internal body cavity may be captured by the image sensor 211, and then transmitted via the bus 2311 to be displayed on the display panel 2313 for examination by the doctor so that a diagnosis can be made. In this embodiment, the output unit 231 is wirelessly connected to the output end 23, for example, via Bluetooth®, ZigBee®, Wi-Fi, or RF etc. Additionally, the output unit 231 may be a display device, a portable electronic device or virtual reality headset. For example, the surgeon may wear a virtual reality headset as the output unit 231 to view images captured by the image sensor 211, however this is not a limitation on the type of the display device 2313 that may be employed.

Figure 6:
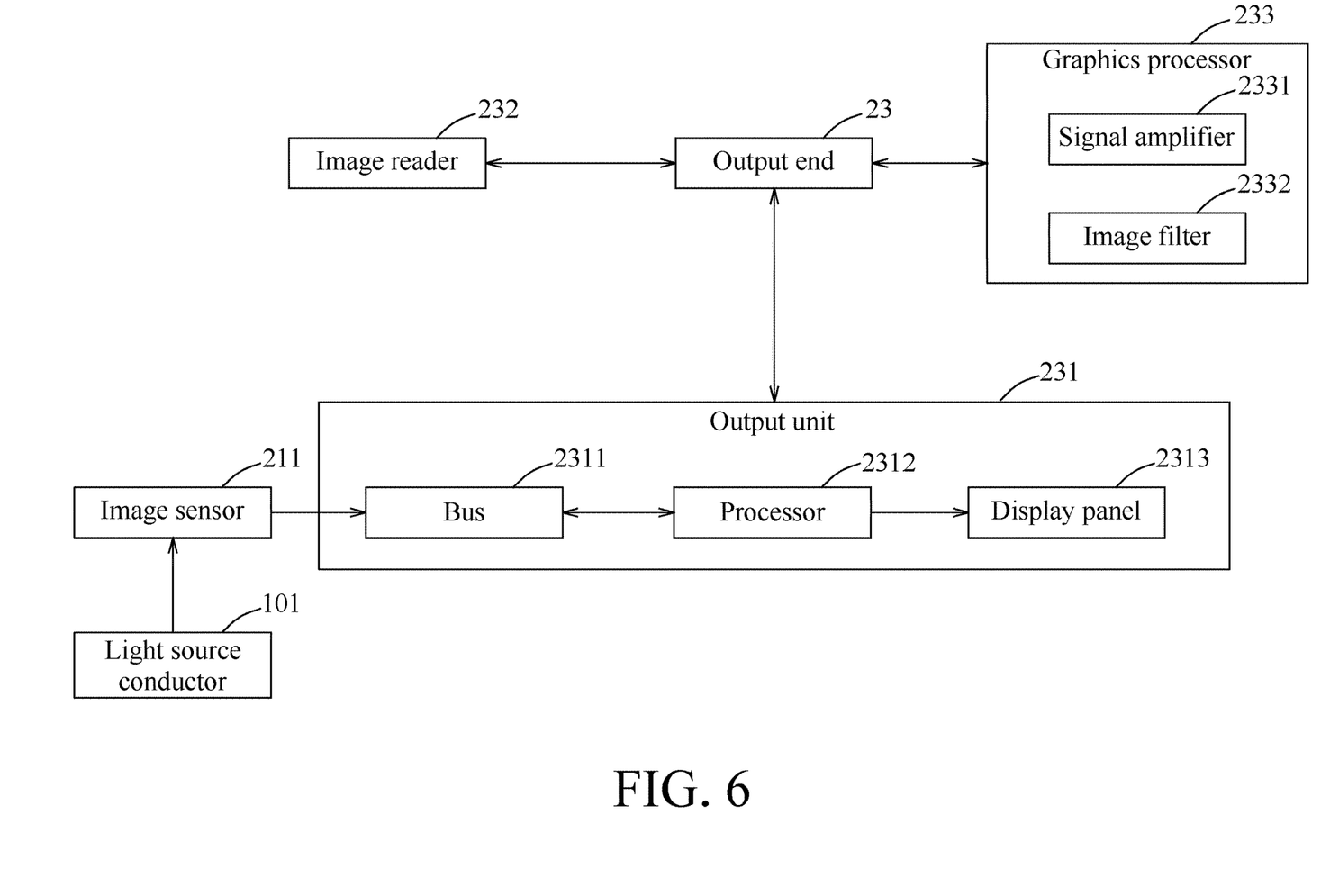
FIG. 6 is a schematic block diagram illustrating image capture and display process of the embodiment.

The image reader 232 is connected to the output end 23, is electrically connected to the image sensor 211, and is used to read the captured image signal from the image sensor 211. The graphics processor 233 is connected to the output end 23 and has a signal amplifier 2331 and an image filter 2332 that are used to process the captured image signal.

In summary of the above, by virtue of the endoscope assembly 1 including the injection needle 10 and the image sensing unit 21, the endoscope assembly 1 can monitor the surgical area while directly performing an injection at the surgical area. The endoscope assembly 1 is therefore convenient to use. Additionally, by the injection needle 10 being in the penetration mode, a clean and even puncture wound can be made on the patient; by the injection needle 10 being in the injection mode a surgical instrument may be extended to the surgical area via the passage 40, thereby obviating the need for a second incision to be made or enlargement of the original incision; by making less and smaller incisions, the length of the patient's postoperative recovery period may be shortened, and the object of this invention has been satisfied.

In the description above, for the purposes of explanation, numerous specific details have been set forth in order to provide a thorough understanding of the embodiments. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. An endoscope assembly comprising:
a base module including an illumination input end;
an injection needle being tubular, being connected to said base module, and having a needle shaft with a longitudinal axis, said needle shaft having a bevel surface that is formed on a distal end thereof, and
an image sensing unit including a tube portion that extends inside said needle shaft in parallel with the longitudinal axis of the needle shaft, and an image sensor that is connected to a distal end of said tube portion and that is adjacent to and inside said bevel surface of said needle shaft, a longitudinal passage being formed between said tube portion and an inner surface of said needle shaft;
wherein said needle shaft of said injection needle further has an end hole formed in said bevel surface;
wherein said injection needle further includes a cylindrical non-liquid filler member that extends through the longitudinal passage in parallel to said tube portion of the imaging sensing unit;

wherein said injection needle is convertible between a penetration mode where said non-liquid filler member extends into said passage up to the end hole without extending beyond the end hole to prevent a patient's skin from clogging the end hole, and an injection mode where said non-liquid filler member is removed from said passage, and a pharmaceutical is injected through the end hole; and wherein said endoscope assembly further comprises a soft tube insertable through said passage and extending out of said end hole when said injection needle is in the injection mode and said non-liquid filler member is removed from said passage, said soft tube being adapted for surgical irrigation or draining.

2. The endoscope assembly as claimed in claim 1, wherein said injection needle further includes a Y-connector that includes:
- a first branch tube having two opposite ends that are respectively connected to said base module and said needle shaft, and that fluidly communicate with said passage; and
- a second branch tube communicating with said first branch tube, and having an injection port that is adapted for inlet of a pharmaceutical therethrough into said passage and outlet of the pharmaceutical from said end hole.

3. The endoscope assembly as claimed in claim 1, wherein said injection needle is removably connected to said base module so that said injection needle is replaceable.

4. The endoscope assembly as claimed in claim 1, wherein:
- said image sensor has an end surface that is perpendicular to an axis of said needle shaft;
- said bevel surface of said needle shaft is inclined relative to said end surface of said image sensor;
- said injection needle further includes an optical component that is made from a transparent material, that is mounted in said needle shaft in front of said image sensor, and that has
  - a light incident side mounted adjacent to and being parallel to said bevel surface of said needle shaft, and adapted to guide light into said optical component, and
  - a light emergent side parallel to and facing said end surface of said image sensor, and adapted to guide light from said light incident side toward said image sensor; and
- said light incident side and said light emergent side form an acute angle therebetween.

5. The endoscope assembly as claimed in claim 4, wherein:
- said optical component is structurally hollow, and has an inner space between said light incident side and said light emergent side; and
- said light emergent side is adapted to guide light that is incident on said light incident side and that is refracted by said inner space to be substantially perpendicular to said end surface of said image sensor.

6. The endoscope assembly as claimed in claim 4, wherein said light incident side is stepped, and has a plurality of spaced-apart first incident surfaces that are parallel to said end surface of said image sensor and that are arranged in a direction parallel to said bevel surface of said needle shaft, each of said first incident surfaces having a length that is not larger than one micrometer.

7. The endoscope assembly as claimed in claim 1, wherein said base module further includes a relay mechanism that is configured as one of an optical fiber light concentrator, a multimedia interface, and an LED light power source.

8. An endoscope system comprising:
- said endoscope assembly as claimed in claim 1, wherein said base module further has an output end; and
- an output unit connected to said output end of said base module of said endoscope assembly, and having a bus that is connected to said image sensing unit via a data connection, a processor that is connected to said bus via a data connection, and a display panel that is electrically connected to said processor;
- wherein said bus is disposed for transmitting an image signal captured by said image sensor, said processor is disposed for receiving the image signal transmitted by said bus and for processing the image signal, and said display panel is disposed for displaying the image signal processed by said processor.

9. The endoscope system as claimed in claim 8, wherein said output unit is connected to said output end of said base module of said endoscope assembly via a wireless connection.

10. The endoscope system as claimed in claim 1 further comprising a light source conductor that is adapted to conduct a light source provided from said illumination input end;
wherein said light source conductor is configured as a plurality of optical fiber strands that are arranged in a circle around a periphery of said image sensor.

* * * * *